United States Patent
Kals

(10) Patent No.: US 9,295,837 B2
(45) Date of Patent: Mar. 29, 2016

(54) OPTIMIZED CHANNEL CONFIGURATION BASED ON SPATIAL PROFILES

(71) Applicant: MED-EL Elektromedizinische Geraete GmbH, Innsbruck (AT)

(72) Inventor: Mathias Kals, Innsbruck (AT)

(73) Assignee: MED-EL Elektromedizinische Geraete GmbH, Inncbruck (AT)

(*) Notice: Subject to any disclaimer, the term of this patent is extended or adjusted under 35 U.S.C. 154(b) by 0 days.

(21) Appl. No.: 14/334,711

(22) Filed: Jul. 18, 2014

(65) Prior Publication Data
US 2015/0025596 A1    Jan. 22, 2015

Related U.S. Application Data

(60) Provisional application No. 61/856,783, filed on Jul. 22, 2013.

(51) Int. Cl.
*A61N 1/00* (2006.01)
*A61N 1/36* (2006.01)

(52) U.S. Cl.
CPC ............................... *A61N 1/36032* (2013.01)

(58) Field of Classification Search
CPC ... A61N 1/36032; A61N 1/0541; H04R 25/50
See application file for complete search history.

(56) References Cited

U.S. PATENT DOCUMENTS

| 2007/0293785 | A1 | 12/2007 | Litvak | A61B 5/00 |
|---|---|---|---|---|
| 2010/0161000 | A1 | 6/2010 | Litvak et al. | 607/57 |
| 2011/0077712 | A1 | 3/2011 | Killian | 607/57 |
| 2012/0179223 | A1 | 7/2012 | Saoji et al. | 607/57 |
| 2015/0088225 | A1* | 3/2015 | Noble et al. | 607/57 |

OTHER PUBLICATIONS

International Searching Authority, International Search Report and Written Opinion—PCT/US2014/047124, date of mailing Nov. 26, 2014, 14 pages.

* cited by examiner

*Primary Examiner* — Robert N Wieland
(74) *Attorney, Agent, or Firm* — Sunstein Kann Murphy & Timbers LLP

(57) ABSTRACT

A cochlear implant arrangement includes an implant electrode having electrode contacts for delivering to adjacent neural tissue electrode stimulation signals for a defined frequency band reflecting tonotopic organization of the cochlea. An implantable stimulation processor is coupled to the implant electrode for producing the electrode stimulation signals. At least one of the electrode contacts is deactivated based on current spread overlap and an electrode masking function of long term average spectra data to avoid delivering electrode stimulation signals to an electrode contact masked by an adjacent electrode contact.

18 Claims, 6 Drawing Sheets

OPTIMIZED CHANNEL CONFIGURATION BASED ON SPATIAL PROFILES

This application claims priority from U.S. Provisional Patent Application 61/856,783, filed Jul. 22, 2013, which is incorporated herein by reference in its entirety.

FIELD OF THE INVENTION

The present invention relates to coding stimulation pulses for cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

Most existing cochlear implant stimulation coding strategies represent a sound signal by splitting it into distinct frequency bands and extracting the envelope (i.e., energy) of each of these bands. These envelope representations of the acoustic signal are used to define the pulse amplitude of stimulation pulses to each electrode. The number of band pass signals typically equals the number of stimulation electrodes, and relatively broad frequency bands are needed to cover the acoustic frequency range. Each electrode contact delivers electric stimulation signals to its adjacent neural tissue for a defined frequency band reflecting the tonotopic organization of the cochlea.

Channel interactions between electrode contacts is caused by the electrically high-conductivity liquid inside the cochlea, and this causes spatial masking. FIG. 2 shows various spatial current spreads based on an exponential spread decay of different intensity on adjacent electrode contacts. An exponential current decay of 0.75 per electrode contact in both directions (apex and base) is assumed, and for convenience, only the spreads caused by the anodic stimulus phases are depicted in FIG. 2. The areas below a given current spread indicate approximately the amount of neuronal recruitments. Electrode contact masking occurs in the areas where current spreads of different electrode contacts overlap. The neurons in these regions are not exclusively related to a specific electrode contact and so are not independent.

When equal neuronal survival across the electrode contacts is given, on average, equal stimuli can be expected to produce equal loudness in a cochlear implant. The upper panel in FIG. 2 illustrates the case where two sequential stimuli on adjacent electrode contacts have the same pulse amplitude. In this case, the masking between these electrode contacts occurs to the same extent and is balanced so that the amount of overlap—the masked area—is equal in both current spreads. On the other hand, when pulse amplitudes of sequential stimuli are different (for equal loudness perception) as shown in the lower panel of FIG. 2, then the electrode contact masking is no longer balanced. The bottom two curves of the lower panel show the case where the current spread of electrode contact 7 is completely covered by the current spread of electrode contact 6. The top two curves of the lower panel show the case where the current spread of electrode contact 6 is completely covered by the current spread of electrode contact 7.

In general, the amount of masking between electrode contacts is a function of their spatial distance and current amplitude. Channels with higher current amplitude will mask neighbouring electrode contacts to some specific extent. The greater the difference in amplitudes between adjacent electrode contacts, the greater will be the resulting masking. If a given electrode contact is completely masked by other electrode contacts, then the related frequency band of that electrode contact cannot be perceived by the implanted listener and is thus missing.

In a conventional cochlear implant fitting procedure, the effectiveness of each electrode contact has to be judged by a skilled audiologist. Each electrode contact has to be assessed in terms of minimum Threshold level (THR) and Maximum Comfort Level (MCL) values, and then further judged in terms of usefulness by the audiologist in cooperation with the implant user (if feasible). The result of this process greatly depends on the skills of the audiologist and the implant user. Electrode contacts with extremely low or high MCL characteristics often are disabled to ensure a reasonable representation of all frequency bands of the sound processor.

SUMMARY OF THE INVENTION

Embodiments of the present invention are directed to a cochlear implant arrangement which includes an implant electrode having electrode contacts for delivering to adjacent neural tissue electrode stimulation signals for a defined frequency band reflecting tonotopic organization of the cochlea. An implantable stimulation processor is coupled to the implant electrode for producing the electrode stimulation signals. At least one of the electrode contacts is deactivated based on current spread overlap and an electrode masking function of long term average spectra data to avoid delivering electrode stimulation signals to an electrode contact masked by an adjacent electrode contact.

The electrode masking function may use average current amplitude values for each electrode contact. The average current amplitude for each electrode contact may represent a non-linear mapping of frequency band and threshold stimulation values for each electrode contact. The electrode masking function may reflect different current decays or equal current decays for each electrode contact. Or the electrode masking function may use average charge values for each electrode contact.

The present hearing situation may include a present sound loudness level. The present hearing situation may be manually selected by the implanted patient, or it may be automatically selected by an external device in communication with the stimulation processor. The external device or the stimulation processor may use the electrode masking function to dynamically deactivate the at least one of the electrode contacts.

Embodiments of the present invention also include a cochlear implant fitting arrangement which includes an electrode measurement module for measuring current spread overlap between electrode contacts of a cochlear implant electrode resulting from delivering electric stimulation signals in a defined frequency band to cochlear neural tissue adjacent to the electrode contacts. An electrode adjustment module deactivates at least one of the electrode contacts based on current spread overlap and an electrode masking function of long term average spectra data to avoid delivering electrode stimulation signals to an electrode contact masked by an adjacent electrode contact.

In such arrangements, the electrode adjustment module may dynamically determine the at least one electrode contact to deactivate based on a defined present hearing situation. The electrode adjustment module may use an electrode masking function based one average current amplitude values for each electrode contact. The average current amplitude for each electrode contact may represent a non-linear mapping of frequency band and threshold stimulation values for each electrode contact. The electrode adjustment module may use an electrode masking function based one average charge values for each electrode contact and/or an electrode masking function reflecting different or equal current decays for each electrode contact.

DETAILED DESCRIPTION OF SPECIFIC EMBODIMENTS

Embodiments of the present invention are directed to an objective approach to an optimised selection of stimulation electrode contacts which helps reduce spatial masking of electrode contacts and ensures a full perceivable presentation of the sound processor frequency range.

As described above, in a typical cochlear implant system, an implantable stimulation processor produces the electrode stimulation signals that are carried by electrode wires in an implant electrode lead to corresponding electrode contacts distributed along the length of the outer surface of an apical end portion of the implant electrode. The electrode contacts deliver the electric stimulation signals to adjacent neural tissue within the cochlea of an implanted patient for perception as sound. Each electrode contact delivers electric stimulation signals to its adjacent neural tissue for a defined frequency band reflecting the tonotopic organization of the cochlea. In embodiments of the present invention, at least one of the electrode contacts is dynamically deactivated based on an electrode masking function of long term average spectra data and current spread overlap for a defined present hearing situation so as to not deliver electric stimulation signals to an electrode contact masked by an adjacent electrode contact.

During fitting of the implant system, masking and masked electrode contacts are identified while receiving stimulation signals in real-life hearing situations. The identified electrode contacts are selectively deactivated for normal post-fitting operation due to their ineffectiveness and the corresponding risk of missing frequency bands, as discussed above. For results of speech perception in implanted listeners, a long-time spectrum (e.g., of speech) can be considered along with the electrical dynamic range (MCL and THR) of each electrode contact in the selection of the electrode contacts. For listening to music or other hearing situations, appropriate long-time spectra also can be considered.

Figure 1:
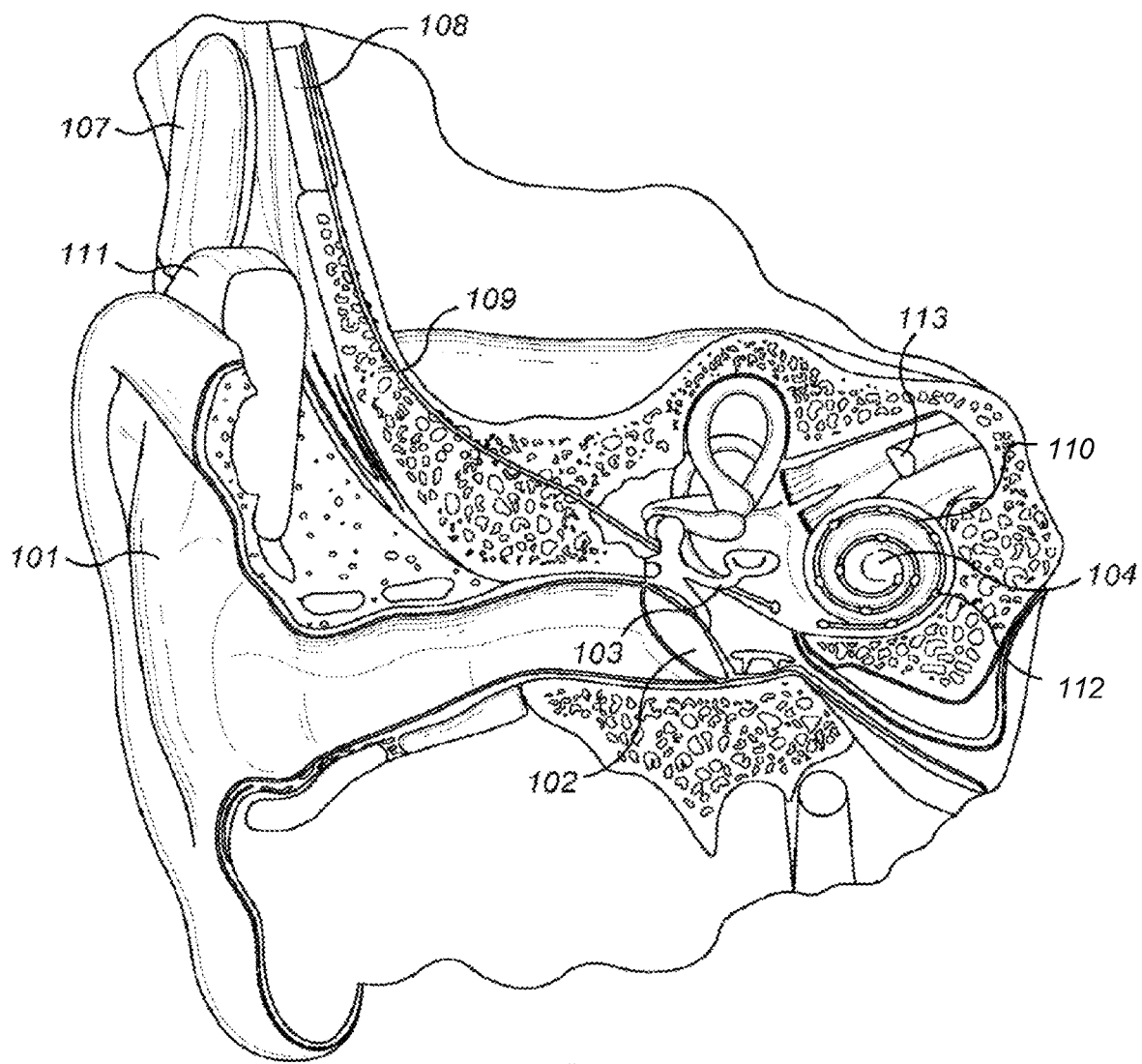
FIG. 1 shows anatomical structures in a human ear having a cochlear implant system.
Figure 2:
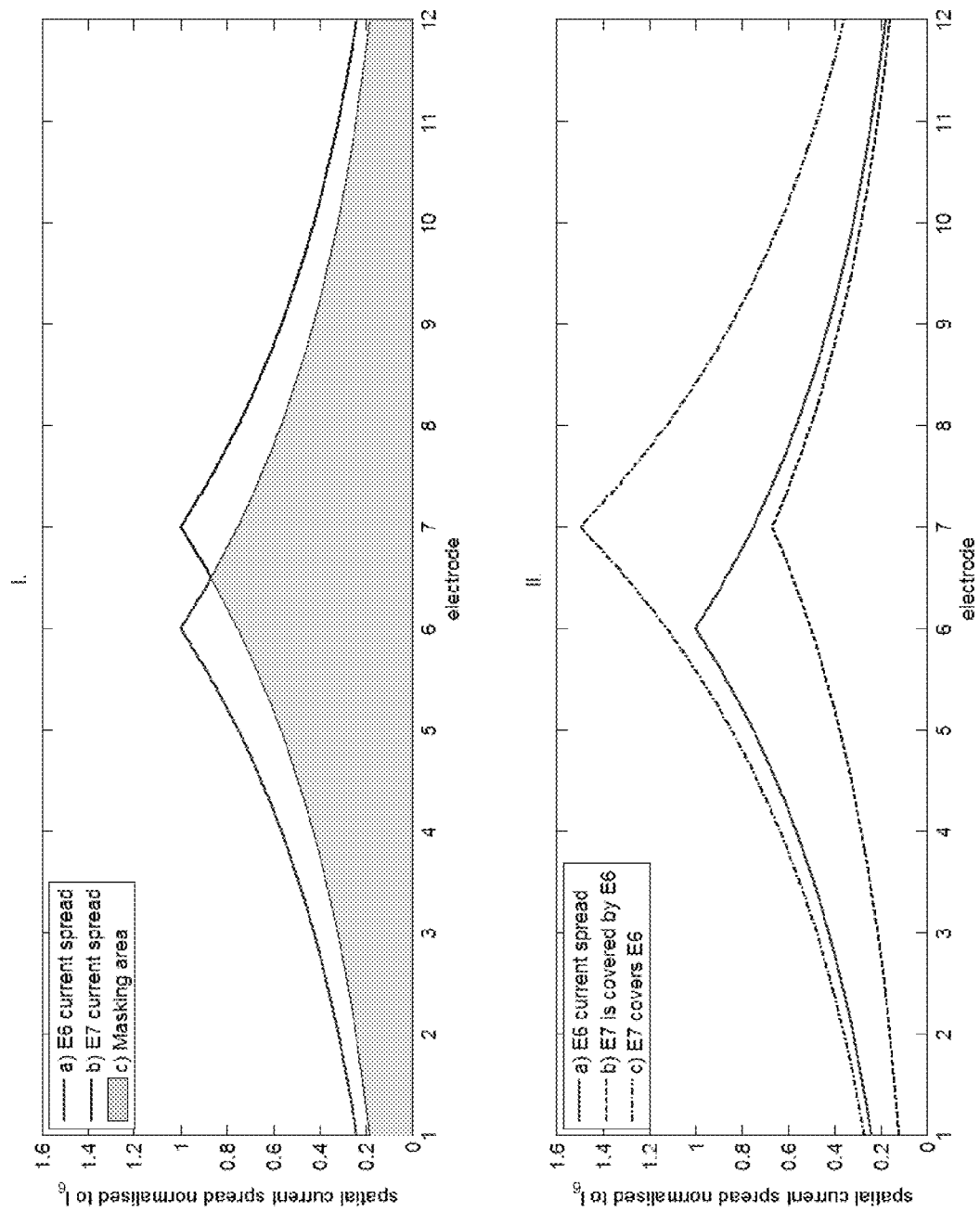
FIG. 2 illustrates the effects of current spread across electrode contacts in an electrode array.
Figure 3:
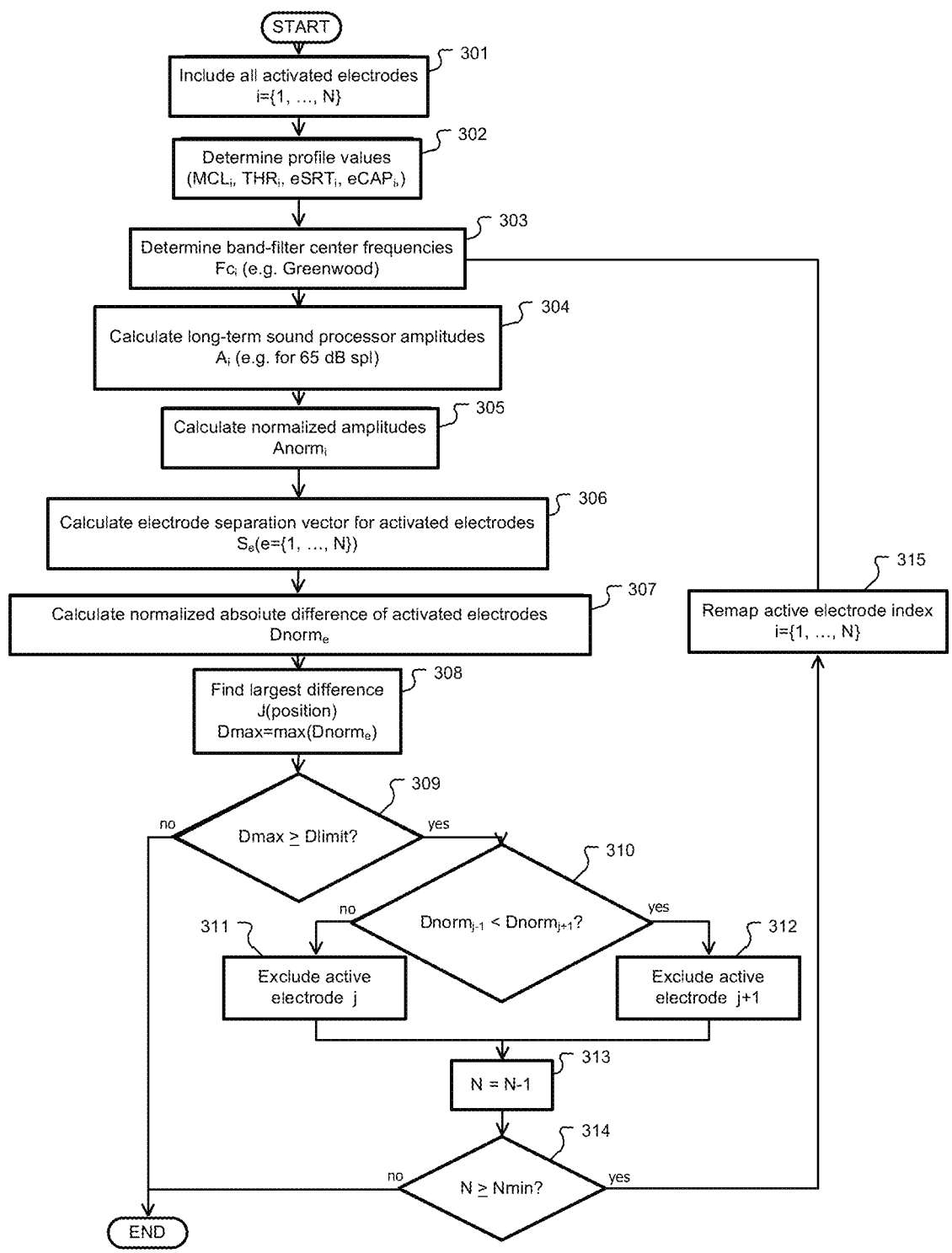
FIG. 3 shows various logical steps in an electrode contact selection algorithm according to one embodiment of the present invention.

FIG. 3 shows various logical steps in an electrode contact selection algorithm according to one embodiment based on an assumption of equal current decays for each electrode contact. In this approach, the absolute value of amplitude derivation for each electrode contact is used as an indicator for electrode contacts with high spatial masking.

Initially, step 301, all activated electrode contacts are included: $i=\{1, \ldots, N\}$ where N denotes the number of activated electrode contacts. Then, step 302, threshold stimulation values $MCL_i$ and $THR_i$ are determined This may be based on direct behavioural measurement or by objective measurement of related neural responses such as $eSRT_i$ (electrically evoked stapedius reflex) or $eCAP_i$ (electrically evoked compound action potential) threshold levels.

To consider spectral properties of speech, long-term average current amplitudes $A_i$ of the sound-processor output are calculated for each frequency band. In this calculation the processor input sound signal is replicated by long-term average speech spectra (Byrne, Denis, et al. "An international comparison of long-term average speech spectra." *Acoustical Society of America Journal* 96 (1994): 2108-2120; incorporated herein by reference), by International Telecommunication Union (ITU) long-term average spectrum, or by any other appropriate speech or sound signal long-term average. The clinically used electrode contact-to-frequency band allocation is used (e.g. Greenwood, 1961) to get corresponding frequency band components $B_i$ of the long-term spectra that are used.

For the frequency band components $B_i$, values at center-frequencies $Fc_i$ or median, mean or any other feasible statistical measure is used, step 303. Based on the frequency band components $B_i$ and behavioural $MCL_i$ and $THR_i$ values, average current amplitudes $A_i$ can be determined, step 304, for example, by IBK amplitude mapping: $A_i=\text{maplaw}(B_i)*(MCL_i-THR_i)+THR_i$, where maplaw is a nonlinear mapping function in a sound processor. In some embodiments, automatic gain control (AGC) and pre-emphasis filter may also be useful in this calculation. These average current amplitudes $A_i$ are calculated for at least one typical acoustic input loudness level, e.g. 65 dB SPL, and average current amplitudes $A_i$ also may be determined for louder and softer sound levels since the proportions within resulting average current amplitudes $A_i$ are varying in dependency of loudness level. By utilizing different types of long-term average spectra at different loudness levels, a selection of accurate electrode contact setups can be performed by the processor automatically based on audio scene analysis to obtain a hearing situation and loudness level detection.

Next, the electrode masking function can be derived based on logarithmizing the frequency-band dependent average stimulation amplitudes $A_i$, step 305, for example, relative to the maximum occurring amplitude as in Equation 1:

$$Anorm_i = 20\log_{10}\left(\frac{A_i}{\max(A_i)}\right) \quad \text{(Equ. 1)}$$

Based on these logarithmized $Anorm_i$ amplitudes, a difference vector $Dabs_e$ (e={1, ..., N−1}) can be calculated by Equation 2:

$$Dabs_e = abs(Anorm_{e+1} - Anorm_e) \quad \text{(Equ. 2)}$$

High values in vector $Dabs_e$ indicate high changes in amplitude between neighbouring electrode contacts. This can serve as an indicator for high masking, assuming equal current decays in both directions (apical and basal).

To consider different spatial distances, when any electrode contacts are deactivated a separation vector $S_e$ is utilized, step 306. This vector represents the spatial distance between neighbouring active electrode contacts, in electrode contact units. So if all electrode contacts (N=12) are activated than $S_e=[1, 1, 1, 1, 1, 1, 1, 1, 1, 1, 1]$ and if electrode contacts 3 and 5 are not activated $S_e=[1, 2, 2, 1, 1, 1, 1, 1]$.

Based on separation vector $S_e$ and difference vector $Dabs_e$, a normalized absolute amplitude difference $Dnorm_e$ can be calculated element-wise by Equation 3, step 307:

$$Dnorm_e = \frac{Dabs_e}{S_e}. \quad \text{(Equ. 3)}$$

High $Dnorm_e$ values indicate relatively large changes in amplitude between neighbouring activated electrode contacts considering their spatial distance.

The position j (j≤e) of highest $Dnorm_e$ value Dmax (the location with highest masking between adjacent activated electrode contacts) is then determined, step 308. Then Dmax is compared to a certain limit Dlimit, step 309. For this limit an empiric value, e.g. Dlimit=4 dB, can be utilized to identify excessively masked or masking electrode contacts. Another variant for Dlimit is a calculation based on statistical properties (e.g. average, median and/or variance) of $Dnorm_e$ values when all electrode contacts are included, as in the first iteration of this algorithm. In Equation 4, two examples based on a median calculation are given. In the first variant an offset Doffset and in the second variant a proportion factor Dprop is used. For Doffset or Dprop empiric values can be used. A combination of both variants is also feasible for determining Dlimit:

Dlimit=median($Dnorm_e$)+Doffset, or

Dlimit=median($Dnorm_e$)*(1+Dprop) (Equ. 4)

If the limit Dlimit is exceeded by Dmax in step 309, then the respective electrode contact should be excluded from stimulation. For this, the values of $Dnorm_{j-1}$ and $Dnorm_{j+1}$ are compared in step 310. If $Dnorm_{j-1} < Dnorm_{j+1}$, then electrode contact j+1 deactivated, step 312, and otherwise electrode contact j is deactivated, step 311. If position j is at the beginning or at the end of the $Dnorm_e$ vector, then electrode contact 1 or N is deactivated, respectively. And either way, the number of electrodes is adjusted to N=N−1, step 313.

After the first iteration, residual active electrode contacts are remapped, step 315, and further iterations of the algorithm are performed until Dmax does not exceed Dlimit (step 309) or some minimum number of enabled electrode channels is reached (e.g. eight channels), step 314.

Figure 4:
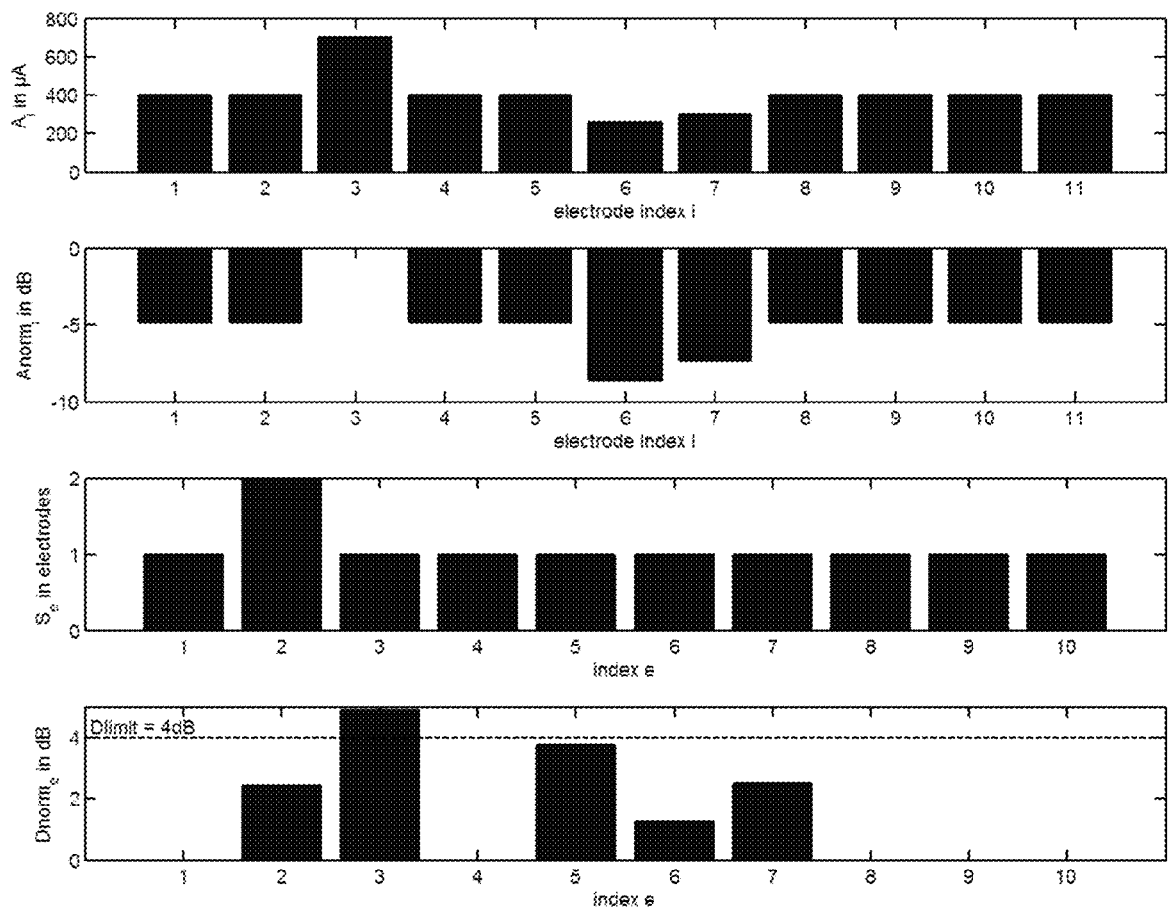
FIG. 4 provides charts of various electrode contact characteristics according to the embodiment of FIG. 3.

An illustration of the resulting amplitudes of this algorithm is given in FIG. 4. In the upper panel of FIG. 4, an arbitrary amplitude distribution of $A_i$ currents is assumed, where electrode contact number 3 in a system of twelve electrode contacts is disabled (N=11). The second panel in FIG. 4 shows calculated $Anorm_i$ amplitudes in dB by Equation 1. The third panel shows distance vector $S_e$ and since only electrode contact 3 is disabled, only $S_2$=2. In the bottom panel of FIG. 4, the resulting $Dnorm_e$ amplitudes from Equations 2 and 3 are shown. When, for example, a Dlimit of 4 dB is used, then just $Dnorm_3$ would exceed the defined limit. The subsequent comparison of neighbouring $Dnorm_2$ and $Dnorm_4$ indicates that $Dnorm_2$ is larger than $Dnorm_4$. Consequently electrode contact number 4 with electrode contact index i=3 needs to be deactivated for less spatial masking. For simplicity in this example, amplitudes A are not recalculated based on the new frequency to electrode contact assignment when an electrode contact is disabled.

Figure 5:
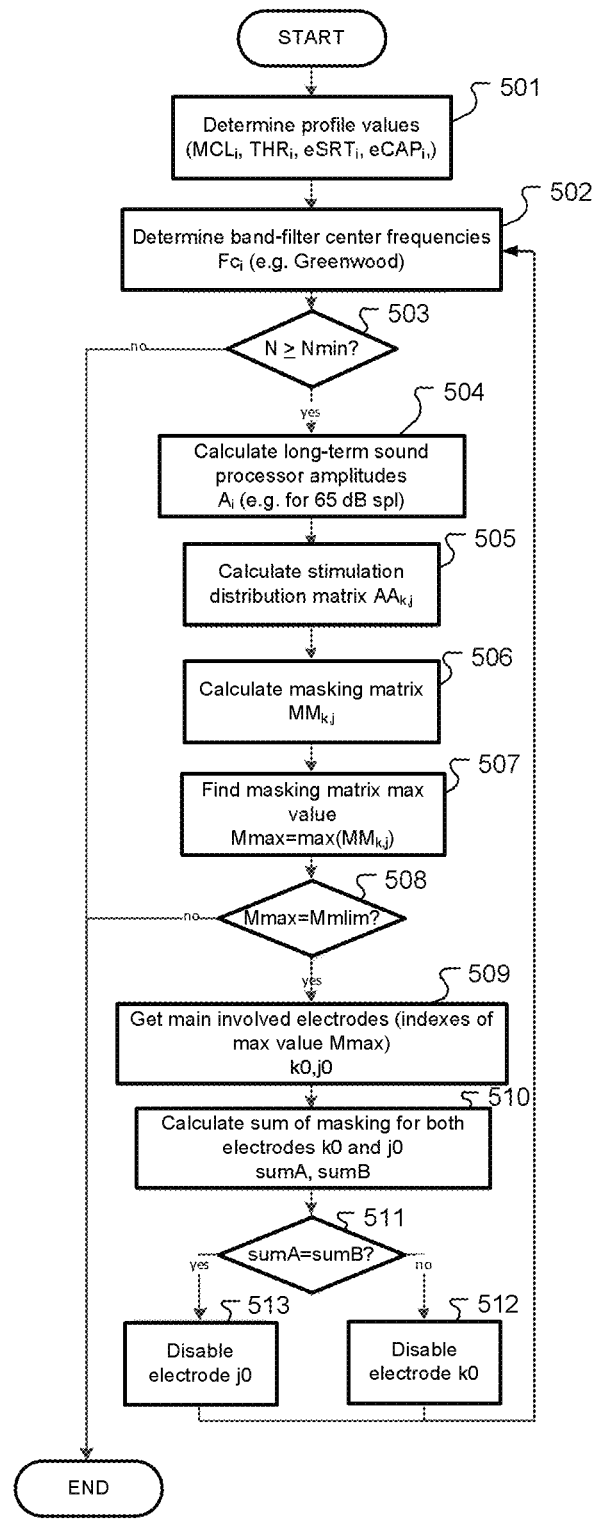
FIG. 5 shows various logical steps in an electrode contact selection algorithm according to another embodiment of the present invention.

To model different current decays along the cochlear in in the apical and basal directions, two different current decay constants $\alpha$ and $\beta$ can be utilised, as described in U.S. Pat. No. 6,594,525 (incorporated herein by reference). Typical values for these current decay parameters are $\alpha$=0.7 and $\beta$=0.6. FIG. 5 shows various logical steps in an electrode contact selection algorithm according to an embodiment of the present invention using such decay constants.

Initially, threshold stimulation values profiles are determined for each electrode contact, step 501, and filter band center frequencies are determined, step 502, as discussed above. So long as the number of selected electrode contacts N>$N_{min}$, step 503 (if not, the process ends as shown), the long-term sound processor amplitudes $A_j$ are calculated as discussed above, step 504.

Alternatively the electrode masking function can be based on using the current decay constants $\alpha$ and $\beta$ to create a stimulation distribution matrix AA (M×M), step 505, by:

$$AA(k, j) = \begin{cases} A(j) \cdot \alpha^{k-j} & \text{if } j < k \\ A(j) & \text{if } j = k \\ A(j) \cdot \beta^{j-k} & \text{if } j > k \end{cases} \quad \text{(Equ. 5)}$$

where M denotes the number of electrode contacts and index j={1, ..., M} and k={1, ..., M} denote the stimulation electrode contact location and resulting stimulation amplitudes at that electrode contact location. Disabled electrode contacts get a value of zero (A(j)=0) in this calculation and have to be excluded from the prior step of frequency to electrode contact allocation.

A row wise normalisation by the diagonal value with:

$$MM(k, j) = 20\log_{10}\left(\frac{AA(k, \{1, \ldots, M\})}{AA(j, j)}\right) \quad \text{(Equ. 6)}$$

leads to a "masking" matrix MM×M) in dB, step 506. In this masking matrix, high values indicate high electrical masking between electrode contacts.

The largest value MMmax (MMmax=MM($k_0$, $j_0$)) in this matrix is searched, step 507. In this search the main diagonal of MM (values are zero per definition) and disabled electrode contacts are not considered. Indexes $k_0$ and $j_0$ of largest found value indicates mainly involved electrode contact numbers.

If the largest found level equal or larger than a certain limit MMlimit (empirical value, e.g. −3 dB), step 508, either electrode contact $k_0$ or $j_0$ will be disabled. For this decision, masking of these two electrode contacts is further investigated. The sum of row $k_0$ and $j_0$, sumA and sumB, is calculated, steps 509 and 510. In this summation the entries of electrode contact $k_0$ and $j_0$ are excluded to evaluate the masking situation when electrode contact $k_0$ or $j_0$ is disabled. When sumA is smaller or equal than sumB, step 511, then electrode contact $j_0$ (corresponds to sumB) will be disabled, step 513, otherwise electrode contact $k_0$, step 512. The procedure starts again until the largest value MMmax is less than MMlimit, step 508.

Figure 6:
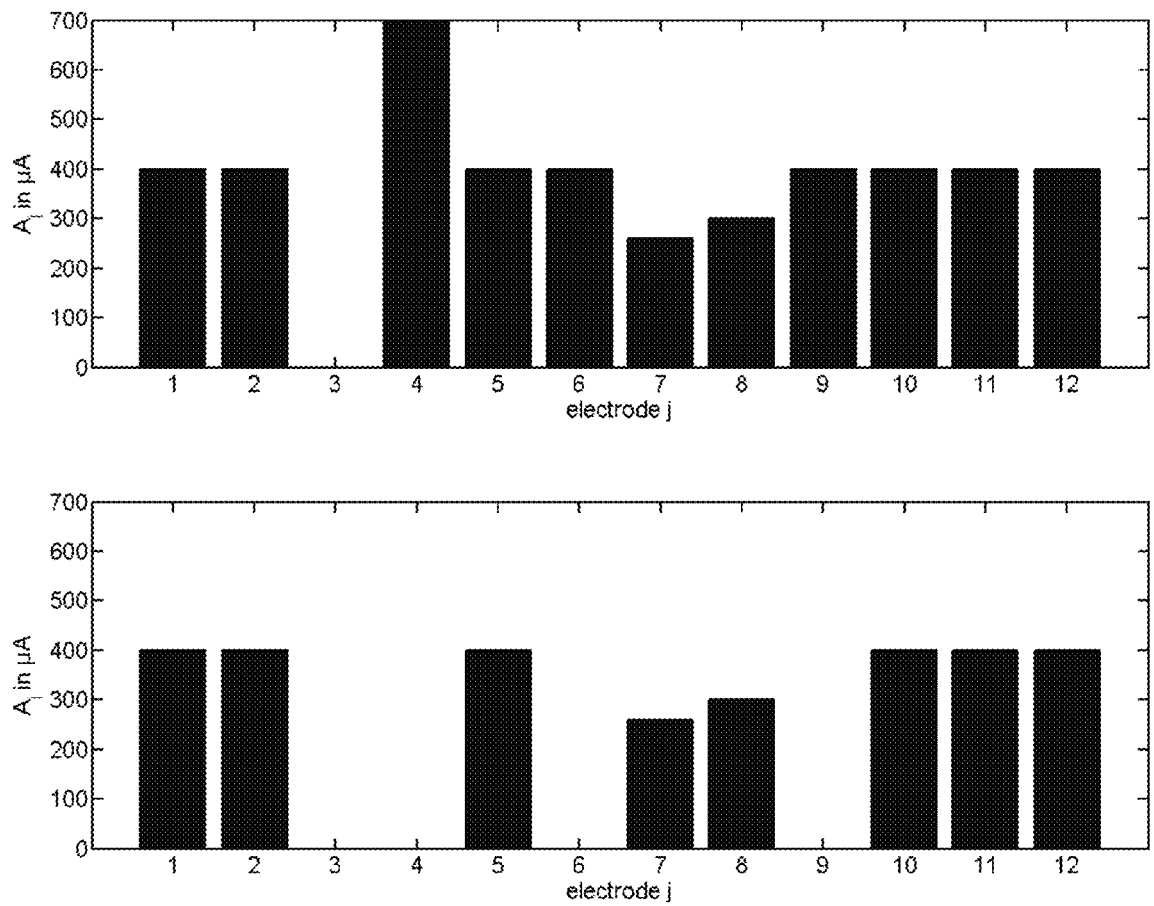
FIG. 6 provides charts of various electrode contact characteristics according to the embodiment of FIG. 5.

A practical example is given in FIG. 6 where the upper panel assumes an arbitrary amplitude distribution of $A_j$ currents, where electrode contact $j=3$ in a system of twelve electrode contact contacts is disabled (M=12). A current decay of $\alpha=0.7$ and $\beta=0.6$ is assumed. When, for example, an MMlimit of −3 dB and a minimum of Nmin=8 enabled channels is used, then this procedure disables electrode contacts 4, 6 and 9 additionally for least electrical masking, as shown in the lower panel of FIG. 6. For simplicity in this example, amplitudes A are not recalculated based on the new frequency to electrode contact assignment when an electrode contact is disabled.

Rather than behavioural threshold fitting values MCL and THR, objective measures such as eCAP or eSRT thresholds can be used saving unnecessary fitting of ineffective channels. Also instead of current levels as such, electric charge values (product of pulse current and time pulse duration) can be used.

In some embodiments, several different shaped spectra may be used for different specific hearing situations. For some hearing styles and situations such different types of music etc. where there is no useful general long-term average spectrum, an arrangement without a shaped spectrum can be used. In commercial embodiments, the system sound processor may be manually switched by the CI-listener (e.g. remote control) or the processor software may switch automatically based on the analysed audio signal spectrum. In general this algorithm can be utilized in an automatic fitting procedure without any user interactions or as a supporting tool for the audiologist while the fitting procedure to ensure an optimal electrode contact configuration.

During a patient fitting process, an objective selection within the available electrode contacts can be performed based on stimulation amplitudes A, user adjustable parameters Nmin (minimum number of enabled electrode contacts—e.g., with a default of ten electrode contacts in a twelve electrode contact system) and Dlimit or MMlimit (e.g., with a default of 4 dB). This ensures that at least a defined minimum of enabled electrode contacts with least masking in the final electrode contact configuration exists. After modifications either in stimulation charge levels, parameters Nmin, Dlimit or MMlimit residual enabled electrode contacts are immediately indicated graphically in a user GUI. In addition to a determination of an optimal channel configuration during the fitting process, some embodiments can also dynamically select the N most effective electrode contacts within each stimulation frame. For this, the selection criterion is inverted since the electrode contacts with outstanding high amplitudes are able to deliver the most important information in a CI-listener.

Similarly, some specific embodiments can be utilized in a free running processor for dynamically determining optimal electrode contact configurations on the fly during stimulation depending on the present acoustic signal. Calculated stimulation amplitudes of the processor can be analysed prior to stimulation. In a sequential stimulation arrangement (e.g., Continuous Interleaved Sampling (CIS)) a certain time period (e.g., one stimulation frame) or a sub group of electrode contacts (e.g., electrode contacts of apical and/or medial and/or basal region) can be considered in the dynamic calculation of optimal electrode contact configuration. For simultaneous stimulation (e.g., Intelligent Parallel (IP) stimulation with Channel Interaction Compensation (CIC)), active electrode contacts within a group of simultaneous electrode contacts can be dynamically determined on the same principle, as described above. The adjustable parameter Nmin also is feasible in such embodiments. In addition, an adjustable parameter N (number of enabled electrode contact) can be used to ensure a constant number of enabled electrode contacts during stimulation.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant arrangement comprising:
   an implant electrode having a plurality of electrode contacts for delivering to adjacent neural tissue electrode stimulation signals for a defined frequency band reflecting tonotopic organization of the cochlea; and
   an implantable stimulation processor coupled to the implant electrode for producing the electrode stimulation signals;
   wherein at least one of the electrode contacts is deactivated based on current spread overlap and an electrode masking function of long term average spectra data to avoid delivering electrode stimulation signals to an electrode contact masked by an adjacent electrode contact; and
   wherein the deactivated electrode contact is dynamically determined based on a defined present hearing situation.

2. A cochlear implant arrangement comprising:
   an implant electrode having a plurality of electrode contacts for delivering to adjacent neural tissue electrode stimulation signals for a defined frequency band reflecting tonotopic organization of the cochlea; and
   an implantable stimulation processor coupled to the implant electrode for producing the electrode stimulation signals;
   wherein at least one of the electrode contacts is deactivated based on current spread overlap and an electrode masking function of long term average spectra data to avoid delivering electrode stimulation signals to an electrode contact masked by an adjacent electrode contact; and
   wherein the electrode masking function uses average current amplitude values for each electrode contact.

3. An arrangement according to claim 2, wherein the average current amplitude for each electrode contact represents a non-linear mapping of frequency band and threshold stimulation values for each electrode contact.

4. A cochlear implant arrangement comprising:
   an implant electrode having a plurality of electrode contacts for delivering to adjacent neural tissue electrode stimulation signals for a defined frequency band reflecting tonotopic organization of the cochlea; and
   an implantable stimulation processor coupled to the implant electrode for producing the electrode stimulation signals;
   wherein at least one of the electrode contacts is deactivated based on current spread overlap and an electrode masking function of long term average spectra data to avoid delivering electrode stimulation signals to an electrode contact masked by an adjacent electrode contact; and
   wherein the electrode masking function uses average charge values for each electrode contact.

5. A cochlear implant arrangement comprising:
   an implant electrode having a plurality of electrode contacts for delivering to adjacent neural tissue electrode stimulation signals for a defined frequency band reflecting tonotopic organization of the cochlea; and
   an implantable stimulation processor coupled to the implant electrode for producing the electrode stimulation signals;
   wherein at least one of the electrode contacts is deactivated based on current spread overlap and an electrode masking function of lon. term average spectra data to avoid delivering electrode stimulation signals to an electrode contact masked by an adjacent electrode contact; and
   wherein the electrode masking function reflects different current decays for each electrode contact.

6. A cochlear implant arrangement comprising:
   an implant electrode having a plurality of electrode contacts for delivering to adjacent neural tissue electrode stimulation signals for a defined frequency band reflecting tonotopic organization of the cochlea; and
   an implantable stimulation processor coupled to the implant electrode for producing the electrode stimulation signals;
   wherein at least one of the electrode contacts is deactivated based on current spread overlap and an electrode masking function of long term average spectra data to avoid delivering electrode stimulation signals to an electrode contact masked by an adjacent electrode contact; and
   wherein the electrode masking function reflects equal current decays for each electrode contact.

7. A method of creating electric stimulation signals for a cochlear implant arrangement, the method comprising:
   providing a plurality of electrode contacts for delivering to adjacent neural tissue electrode stimulation signals for a defined frequency band reflecting tonotopic organization of the cochlea; and
   deactivating at least one of the electrode contacts based on current spread overlap and an electrode masking function of long term average spectra data to avoid delivering electrode stimulation signals to an electrode contact masked by an adjacent electrode contact;
   wherein the deactivated electrode contact is dynamically determined based on a defined present hearing situation.

8. A method of creating electric stimulation signals for a cochlear implant arrangement, the method comprising:
   providing a plurality of electrode contacts for delivering to adjacent neural tissue electrode stimulation signals for a defined frequency band reflecting tonotopic organization of the cochlea; and
   deactivating at least one of the electrode contacts based on current spread overlap and an electrode masking function of long term average spectra data to avoid delivering electrode stimulation signals to an electrode contact masked by an adjacent electrode contact;
   wherein the electrode masking function uses average current amplitude values for each electrode contact.

9. A method according to claim 8, wherein the average current amplitude for each electrode contact represents a non-linear mapping of frequency band and threshold stimulation values for each electrode contact.

10. A method of creating electric stimulation signals for a cochlear implant arrangement, the method comprising:
    providing a plurality of electrode contacts for delivering to adjacent neural tissue electrode stimulation signals for a defined frequency band reflecting tonotopic organization of the cochlea; and
    deactivating at least one of the electrode contacts based on current spread overlap and an electrode masking function of long term average spectra data to avoid delivering electrode stimulation signals to an electrode contact masked by an adjacent electrode contact;
    wherein the electrode masking function uses average charge values for each electrode contact.

11. A method of creating electric stimulation signals for a cochlear implant arrangement, the method comprising:
- providing a plurality of electrode contacts for delivering to adjacent neural tissue electrode stimulation signals for a defined frequency band reflecting tonotopic organization of the cochlea; and
- deactivating at least one of the electrode contacts based on current spread overlap and an electrode masking function of long term average spectra data to avoid delivering electrode stimulation signals to an electrode contact masked by an adjacent electrode contact;
- wherein the electrode masking function reflects different current decays for each electrode contact.

12. A method of creating electric stimulation signals for a cochlear implant arrangement, the method comprising:
- providing a plurality of electrode contacts for delivering to adjacent neural tissue electrode stimulation signals for a defined frequency band reflecting tonotopic organization of the cochlea; and
- deactivating at least one of the electrode contacts based on current spread overlap and an electrode masking function of long term average spectra data to avoid delivering electrode stimulation signals to an electrode contact masked by an adjacent electrode contact;
- wherein the electrode masking function reflects equal current decays for each electrode contact.

13. A cochlear implant fitting arrangement comprising:
- an electrode measurement module for measuring current spread overlap between electrode contacts of a cochlear implant electrode resulting from delivering electric stimulation signals in a defined frequency band to cochlear neural tissue adjacent to the electrode contacts; and
- an electrode adjustment module for deactivating at least one of the electrode contacts based on current spread overlap and an electrode masking function of long term average spectra data to avoid delivering electrode stimulation signals to an electrode contact masked by an adjacent electrode contact;
- wherein the electrode adjustment module dynamically determines the at least one electrode contact to deactivate based on a defined present hearing situation.

14. A cochlear implant fitting arrangement comprising:
- an electrode measurement module for measuring current spread overlap between electrode contacts of a cochlear implant electrode resulting from delivering electric stimulation signals in a defined frequency band to cochlear neural tissue adjacent to the electrode contacts; and
- an electrode adjustment module for deactivating at least one of the electrode contacts based on current spread overlap and an electrode masking function of long term average spectra data to avoid delivering electrode stimulation signals to an electrode contact masked by an adjacent electrode contact;
- wherein the electrode adjustment module use an electrode masking function based one average current amplitude values for each electrode contact.

15. A fitting arrangement according to claim 14, wherein the average current amplitude for each electrode contact represents a non-linear mapping of frequency band and threshold stimulation values for each electrode contact.

16. A cochlear implant fitting arrangement comprising:
- an electrode measurement module for measuring current spread overlap between electrode contacts of a cochlear implant electrode resulting from delivering electric stimulation signals in a defined frequency band to cochlear neural tissue adjacent to the electrode contacts; and
- an electrode adjustment module for deactivating at least one of the electrode contacts based on current spread overlap and an electrode masking function of long term average spectra data to avoid delivering electrode stimulation signals to an electrode contact masked by an adjacent electrode contact;
- wherein the electrode adjustment module uses an electrode masking function based one average charge values for each electrode contact.

17. A cochlear implant fitting arrangement comprising:
- an electrode measurement module for measuring current spread overlap between electrode contacts of a cochlear implant electrode resulting from delivering electric stimulation signals in a defined frequency band to cochlear neural tissue adjacent to the electrode contacts; and
- an electrode adjustment module for deactivating at least one of the electrode contacts based on current spread overlap and an electrode masking function of long term average spectra data to avoid delivering electrode stimulation signals to an electrode contact masked by an adjacent electrode contact;
- wherein the electrode adjustment module uses an electrode masking function reflecting different current decays for each electrode contact.

18. A cochlear implant fitting arrangement comprising:
- an electrode measurement module for measuring current spread overlap between electrode contacts of a cochlear implant electrode resulting from delivering electric stimulation signals in a defined frequency band to cochlear neural tissue adjacent to the electrode contacts; and
- an electrode adjustment module for deactivating at least one of the electrode contacts based on current spread overlap and an electrode masking function of long term average spectra data to avoid delivering electrode stimulation signals to an electrode contact masked by an adjacent electrode contact;
- wherein the electrode adjustment module uses an electrode masking function reflecting equal current decays for each electrode contact.

* * * * *

UNITED STATES PATENT AND TRADEMARK OFFICE
CERTIFICATE OF CORRECTION

PATENT NO.         : 9,295,837 B2
APPLICATION NO.    : 14/334711
DATED              : March 29, 2016
INVENTOR(S)        : Mathias Kals Page 1 of 1

It is certified that error appears in the above-identified patent and that said Letters Patent is hereby corrected as shown below:

Claims

In Col. 9, line 67, claim 5
replace "lon. term"
with --long term--

In Col. 12, line 2, claim 14
replace "one"
with --on--

In Col. 12, line 21, claim 16
replace "one"
with --on--

Signed and Sealed this
Fourteenth Day of June, 2016

Michelle K. Lee
*Director of the United States Patent and Trademark Office*